US009820928B1

(12) United States Patent
Bellovin et al.

(10) Patent No.: US 9,820,928 B1
(45) Date of Patent: Nov. 21, 2017

(54) MODIFIED POLYSACCHARIDES

(71) Applicant: Corn Products Development, Inc., Sao Paulo (BR)

(72) Inventors: Christopher Bellovin, Bridgewater, NJ (US); Larisa Sheihet, Bridgewater, NJ (US); Nikola Nikolic, Bridgewater, NJ (US)

(73) Assignee: Corn Products Development, Inc., Jabaquara, Sao Paulo (BR)

( * ) Notice: Subject to any disclaimer, the term of this patent is extended or adjusted under 35 U.S.C. 154(b) by 0 days.

(21) Appl. No.: 15/140,107

(22) Filed: Apr. 27, 2016

(51) Int. Cl.
| | | |
|---|---|---|
| A61K 8/00 | (2006.01) | |
| A61K 8/18 | (2006.01) | |
| A61Q 5/00 | (2006.01) | |
| A61Q 9/00 | (2006.01) | |
| A61K 8/73 | (2006.01) | |
| C08B 31/00 | (2006.01) | |
| C08B 37/00 | (2006.01) | |
| A61Q 5/02 | (2006.01) | |
| A61Q 5/12 | (2006.01) | |
| A61Q 19/10 | (2006.01) | |
| A61Q 5/06 | (2006.01) | |
| A61Q 19/00 | (2006.01) | |
| C09D 105/00 | (2006.01) | |

(52) U.S. Cl.
CPC .............. *A61K 8/737* (2013.01); *A61K 8/732* (2013.01); *A61Q 5/02* (2013.01); *A61Q 5/06* (2013.01); *A61Q 5/12* (2013.01); *A61Q 19/007* (2013.01); *A61Q 19/10* (2013.01); *C08B 31/006* (2013.01); *C08B 37/0096* (2013.01); *C09D 105/00* (2013.01); *A61K 2800/30* (2013.01); *A61K 2800/34* (2013.01)

(58) Field of Classification Search
CPC .............. C09D 105/00; A61K 2800/34; A61K 2800/30
See application file for complete search history.

(56) References Cited

U.S. PATENT DOCUMENTS

| | | | |
|---|---|---|---|
| 4,758,282 A | 7/1988 | Stober et al. | |
| 4,992,538 A | 2/1991 | Sau | |
| 6,066,727 A | 5/2000 | Yamamoto et al. | |
| 6,398,911 B1 | 6/2002 | Schroeder et al. | |
| 6,703,027 B2 | 3/2004 | Kurosawa et al. | |
| 6,743,760 B1 | 6/2004 | Hardy et al. | |
| 6,897,189 B2 | 5/2005 | Dupont et al. | |
| 7,528,101 B2 | 5/2009 | Carvell et al. | |
| 7,947,258 B2 | 5/2011 | Terada | |
| 7,949,258 B2 | 5/2011 | Fukuda | |
| 7,967,871 B2 | 6/2011 | Gibbs et al. | |
| 8,147,812 B2 | 4/2012 | Peffly et al. | |
| 8,242,097 B2 | 8/2012 | Philippe | |
| 8,450,294 B2 | 5/2013 | Lepilleur et al. | |
| 2006/0124553 A1* | 6/2006 | Taylor ................... | C02F 1/5263 210/698 |
| 2007/0269397 A1 | 11/2007 | Terada | |
| 2007/0269398 A1* | 11/2007 | Terada ................... | A61K 8/737 424/70.122 |
| 2008/0209645 A1 | 9/2008 | Carrillo et al. | |
| 2008/0306253 A1 | 12/2008 | Harrison et al. | |
| 2010/0247472 A1 | 9/2010 | Sau | |
| 2013/0129639 A1 | 5/2013 | Anderson et al. | |
| 2014/0076345 A1 | 3/2014 | Fujii et al. | |
| 2014/0127149 A1 | 5/2014 | Lepilleur et al. | |
| 2014/0166034 A1 | 6/2014 | Morioka | |
| 2014/0335041 A1 | 11/2014 | Peffly et al. | |

FOREIGN PATENT DOCUMENTS

| | | |
|---|---|---|
| EP | 0898960 B1 | 7/2001 |
| EP | 1862160 B1 | 2/2013 |
| JP | 2005082796 | 3/2005 |
| WO | WO2010000090 A2 | 1/2010 |
| WO | 2010111576 A1 | 9/2010 |
| WO | WO2014111578 A1 | 7/2014 |
| WO | WO 2014/185275 * | 11/2014 |
| WO | WO2014177294 A1 | 11/2014 |
| WO | WO20150159059 A1 | 2/2015 |

OTHER PUBLICATIONS

Konishi et al., WO 2014/185275, published: Nov. 20, 2014; English machine translation obtained on Jan. 22, 2017.*

* cited by examiner

*Primary Examiner* — Johann R Richter
*Assistant Examiner* — Genevieve S Alley
(74) *Attorney, Agent, or Firm* — Jason Grauch; Jacqueline Cohen

(57) ABSTRACT

Cationic and silicon substituents are introduced into polysaccharides thereby producing modified polysaccharides cationically substituted by quaternary ammonium groups and having a charge density of about 0.1 to about 2.5 meq/g, and further substituted by siliconate groups such that the modified polysaccharide has a silicon content of about 300 to about 5000 ppm. The modified polysaccharides have application in industrial, home care and personal care surface modifying formulations.

10 Claims, No Drawings

MODIFIED POLYSACCHARIDES

BACKGROUND OF THE INVENTION

Field of the Invention

The present invention is directed towards modified polysaccharides. More particularly, the present invention is directed towards modified polysaccharides having both cationic and organo-functional silane constituents, as well as surface modifying compositions containing such modified polysaccharides.

Water soluble polysaccharides find broad industrial application as rheology modifiers, film formers and binders. They are widely used as thickeners to control the rheology of various water-based formulations, such as latex paints, drilling muds, cosmetics, detergents and building materials. Natural polysaccharides such as cellulose, guar and starch are a large class of commercial water soluble polymers. Common commercially available chemically modified natural polysaccharides include compounds such as Polyquaternium-10 (cationically modified hydroxyethylcellulose) and guar hydroxypropyltrimonium chloride (cationically modified guar gum). Such polysaccharides are often used in surface modifying compositions.

Surface modifying compositions containing various combinations of surfactants, conditioning agents and carriers are known. Such surface modifying compositions have application in a wide variety of uses, including industrial, household products, and personal care. These products typically comprise an anionic surfactant in combination with a conditioning agent such as a cationic conditioning polymer, a silicone, a hydrocarbon oil, a fatty ester, or combinations thereof.

Cationic conditioning polymers can act as conditioning and surface modifying agents in surface modifying compositions. These polymeric conditioners help the substrate to which they are applied look and feel better by improving the physical condition of these surfaces (hence, the name "conditioning" in that they improve the surface of a substrate). For example, when the substrate is keratin or hair, the conditioner can make dry hair feel smoother, shinier and more manageable. When the substrate is skin, cationic conditioners can serve a variety of functions such as moisturizing and protection from the environment. When the substrate is wood or other cellulosic material such as paper, the conditioners can aid in protecting or preserving the material. Examples of substrates onto which compositions containing cationic conditioning polymers can be applied include hair, skin, nails, keratin containing substrate, hard surface, carpet, fabric, leather, wood, plastic containing composition, and vinyl.

Among the ways in which some of these conditioning polymers work is through substantivity onto the substrate. Cationic conditioning polymers achieve substantivity to the substrate through a cationic charge that promotes binding to the innate anionic charge of the substrate to which it is applied. Depending on the nature of the substrate, substantivity of the polymer onto the substrate can provide a film or barrier function. Other benefits include enhanced deposition of ingredients and improved feel. Such ingredients can include silicone.

Silicones, or more precisely polysiloxanes, consist of an inorganic silicon-oxygen backbone chain ( . . . —Si—O—Si—O—Si—O— . . . ) with organic side groups attached thereto and have the general formula $[R_2SiO]_n$ wherein R is an organic group such as methyl, ethyl or phenyl. The most common siloxane is polydimethylsiloxane (a/k/a PDMS or Dimethicone), a clear silicone oil. Silicones present in surface modifying compositions, like cationic conditioning polymers, can also serve a variety of functions, including acting as a defoamers and improving the feel and appearance of a substrate, making it smoother and shinier. However, silicones can be incompatible with typical surface modifying compositions, and tend to separate due to their low specific gravity.

In leave-on formulations such as wax emulsions, one function of cationic polymers in the formulations is film forming (i.e., providing a protective coating). Such wax emulsions are useful in a variety of applications, including paints/lacquers, printing inks, textiles, floor polishes, wood and timber protection, automobile polishes, and paper and board coatings.

In rinse-off formulations containing silicones, one function of cationic polymers in the formulations is to aid in deposition of ingredients such as silicone onto the substrate to which it is applied. Polyquaternium-10 is an example of a common conditioning polymer used to aid in deposition of silicone onto the surface of the substrate (e.g., hair, skin or other anionically-charged surfaces).

Unfortunately, once deposited silicone can be difficult to remove. This deposition results in buildup with each consecutive application. When applied by shampooing, such buildup can reduce the volume of the desired hair style, resulting in a 'droopy' and flat hair style.

Attempted solutions to avoiding buildup have included treating the hair with water-in-water emulsions containing cationic polymers with soluble salts in surfactant compositions. Clarifying shampoos can also be used; however, use of these shampoos on colored hair can cause the hair color to fade faster. Low viscosity microemulsified silicone oils can be combined with cationic polymers; however, these are less effective for difficult to manage hair. Accordingly, there remains a need for silicone-containing surface modifying compositions that provide the benefits of silicone without its associated problems such as buildup.

BRIEF SUMMARY OF THE INVENTION

Provided herein is a modified polysaccharide having both cationic and silicon substituents. This modified polysaccharide is cationically substituted with quaternary ammonium groups and has a charge density of about 0.1 to about 2.5 meq/g. More preferably, the polysaccharide substituted by quaternary ammonium groups has a charge density of about 0.2 to about 2.0 meq/g. Even more preferably, the polysaccharide substituted by quaternary ammonium groups has a charge density of about 0.8 to about 1.5 meq/g.

Quaternary ammonium groups useful in the modified polysaccharide are derived from a quaternary ammonium compound according to one of the general formulae (I) or (II):

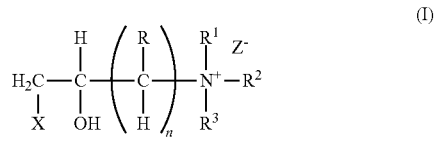

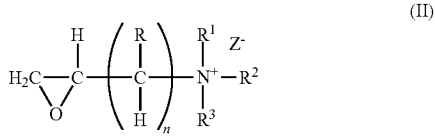

wherein n is an integer from 1 to 16, preferably 1;

X is halogen, particularly fluorine, chlorine, bromine or iodine, and preferably chlorine;

$Z^-$ is an anion which may be inorganic, for example, halide (fluoride, chloride, bromide or iodide, preferably chloride), nitrate, nitrite; phosphate or hydroxide, or organic, for example carboxylate such as acetate or propionate;

R is hydrogen or methyl, preferably hydrogen;

$R^1$, $R^2$ and $R^3$, which may be the same or different, are each an organic radical, preferably containing up to 10 carbon atoms, with $R^1$, $R^2$ and $R^3$ each preferably methyl.

Preferably, the quaternary ammonium compound is glycidyltrimethylammonium chloride or its equivalent.

The modified polysaccharide is also substituted with siliconate groups, resulting in a modified polysaccharide having a silicon content of about 300 to about 5000 ppm. Preferably, the ratio of cationic substituents to silicon substituents on the polysaccharide is from about 1500:1 to about 1:3. In a preferred embodiment, the silicon substituent is an alkyl silanol, more preferably methyl silanol.

In one embodiment the modified polysaccharide described herein can further be crosslinked to reduce its solubility in water.

An example of a suitable polysaccharide useful for modification according to the present invention is a polygalactomannan. Useful polygalactomannans include fenugreek gum, guar gum, tara gum, locust bean gum and cassia gum. In one embodiment, the polygalactomannan is guar gum. In another embodiment, the polygalactomannan is tara gum.

Modified polysaccharides described herein have application in industrial, home care and personal care surface modifying or cleansing formulations. For example, a surface modifying composition according to the present invention can comprise from about 0.1 wt % to about 1.0 wt % by weight of the composition of a cationically modified and silicone grafted polysaccharide; from about 5 wt % to about 60 wt % by weight of the composition of at least one surfactant; and a carrier.

In one embodiment, the cationically modified and silicone grafted polysaccharide used in the surface modifying composition is a cationically modified and silicone grafted polygalactomannan. Examples of base polygalactomannans useful forming the modified polysaccharide used in the surface modifying composition include fenugreek gum, guar gum, tara gum, locust bean gum, cassia gum and combinations thereof. In a preferred embodiment, the polygalactomannan is guar gum.

In another embodiment, the cationically modified and silicone grafted polysaccharide used in the surface modifying composition is a cationically modified and silicone grafted starch. Starches and flours useful in the present invention can be chosen from any native source. Native sources include banana, corn, pea, potato, sweet potato, barley, wheat, rice, sago, amaranth, tapioca, sorghum, waxy maize, waxy rice, waxy barley, waxy potato, waxy sorghum, starches containing high amylose, and the like. Preferred starches are low amylose or waxy starches, including waxy maize, waxy rice, waxy potato, waxy sorghum, waxy cassava and waxy barley. Unless specifically distinguished, references to starch in this description are meant to include their corresponding flours. References to starch are also meant to include starch containing protein, whether the protein is endogenous protein or protein added from an animal or plant source such as zein, albumin, and soy protein.

Surface modifying compositions according to the present invention can use a variety of one or more surfactants. Such surfactants include anionic surfactants, cationic surfactants, nonionic surfactants, amphoteric surfactants and combinations thereof.

The present invention further provides a method of achieving a modified substrate wherein the surface modifying composition described above is applied to the substrate. Such substrates can vary depending upon the type of surface modifying composition used (e.g., industrial, home care or personal care). For example, when the surface modifying composition is a personal care composition, the substrate can be a keratinaceous surface (e.g., hair, nail or skin). When the surface modifying composition is a film forming composition, the substrate can be wood, cellulose, ceramic, glass, metallic or any other anionically charged material.

DETAILED DESCRIPTION OF THE INVENTION

As used herein "consumer product" means baby care, beauty care, fabric & home care, family care, feminine care, health care, products or devices generally intended to be used or consumed in the form in which it is sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, and tooth whitening.

As used herein, the term "surface modifying composition" refers to a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, Illustrated above is the chemical structure of cellulose, wherein R is H, or hydroxyethylcellulose, wherein at least one R is $CH_2CH_2OH$.

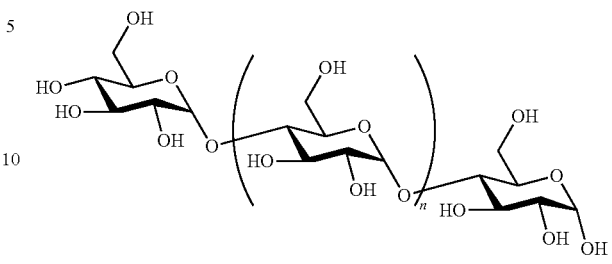

The above chemical structure is that of starch (amylose molecule). For the purpose of the present invention, waxy starches (amylopectin molecules) are also anticipated to have utility, as well as a combination of both amylose and amylopectin molecules.

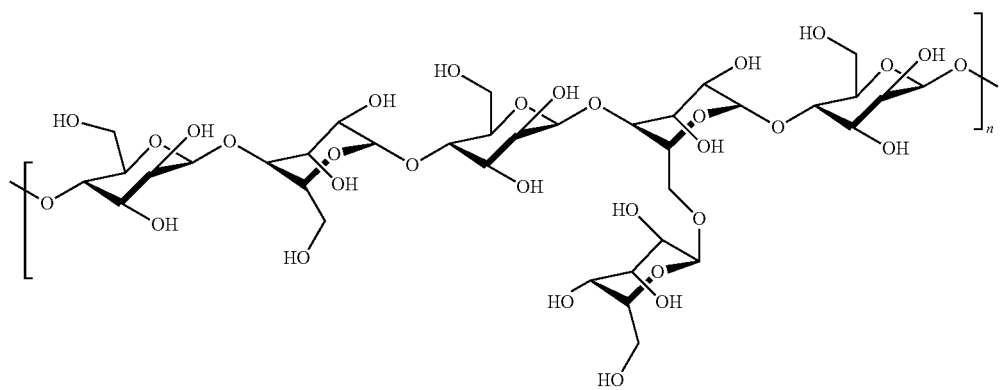

car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

Polysaccharides useful in preparing the modified polysaccharides according to the present invention include a variety of sources from cellulose to starch to polygalactomannans such as fenugreek gum, guar gum, tara gum, locust bean gum and cassia gum. The following structures are illustrative of various polysaccharides suitable for modification according to the present invention—

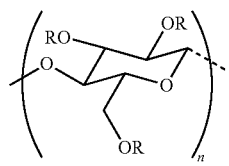

Illustrated above is the chemical structure of cassia gum. In addition to molecular weight, cassia gum differs from other gums such as tara gum and guar gum in the ratio of mannose to galactose. From the above structure it is seen that cassia gum has a mannose:galactose ratio of 5:1. In contrast, the mannose:galactose ratio of locust gum is 4:1, tara gum is 3:1, and guar gum is 2:1.

When the polysaccharide is a starch, the source of starch prior to chemical modification can be chosen from a variety of sources such as tubers, legumes, cereal, and grains. Non-limiting examples of this starch source include corn starch, wheat starch, rice starch, waxy corn starch, oat starch, cassava starch, waxy barley, waxy rice starch, glutenous rice starch, sweet rice starch, potato starch, tapioca starch, sago starch, or mixtures thereof. Preferred starch sources are low amylose or waxy starches, including waxy maize, waxy rice, waxy potato, waxy sorghum, waxy cassava and waxy barley.

The above source or base polysaccharides can be in their native form or a modified form. Modified forms or derivatives include physically, enzymatically or chemically modified polysaccharides. Non-limiting examples of such modifications include thermal modification, acid modification, oxidation, pyroconversion, crosslinking, acetylation, esterification, hydroxyethylation, hydroxypropylation, phosphorylation, succinate modification, and carboxymethylation among others.

From the above structures it is seen that polysaccharides used as the precursors for cationic and silicon modification contain hydroxyl functional groups as part of their structure. These reactive groups are available for a wide range of chemical reactions, such as etherification or esterification. In the case of cationic moieties, quaternary ammonium groups can be grafted onto the polymer backbone and become covalently bound. These cationic groups enhance the polysaccharide's attachment to anionic substrates, such as hair and skin.

Cationic substituents can be introduced into the polysaccharide molecule by reacting the polysaccharide—preferably in the presence of a catalyst, and typically by an etherification or esterification reaction—with one or more reagents containing a cationic group, such as a quaternary ammonium, sulfonium or phosphonium group. Preferably the reaction is an etherification reaction and the reagent is a quaternary ammonium reagent.

When the reagent is a quaternary ammonium reagent, polysaccharides according to the present invention are prepared by reacting the polysaccharide with a quaternary ammonium salt having a reactive chemical end-group in the presence of a base and in an aqueous or solvent-based medium. Suitable quaternary ammonium compounds can be represented by one of the following general formulae (I) and (II)—

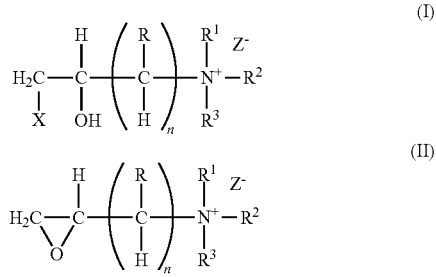

wherein
n is an integer from 1 to 16, preferably 1;
X is halogen, particularly fluorine, chlorine, bromine or iodine, and preferably chlorine;
$Z^-$ is an anion which may be inorganic, for example, halide (fluoride, chloride, bromide or iodide, preferably chloride), nitrate, nitrite; phosphate, sulfate or hydroxide; or organic, for example, carboxylate such as acetate or propionate;
R is hydrogen or methyl, preferably hydrogen;
$R^1$, $R^2$ and $R^3$, which may be the same or different, are each an organic radical containing up to 10 carbon atoms, preferably methyl.

Many compounds having the above formulae are known or can be prepared by conventional procedures. Some such compounds are commercially available. Examples of suitable quaternary ammonium compounds include:
2,3-epoxypropyl-N,N,N-trimethylammonium chloride (a/k/a glycidyltrimethylammonium chloride (commercially available from SKW Quab Chemicals Inc. as a 70% aqueous solution under the name QUAB 151)); and
3-chloro-2-hydroxypropyl-N,N,N-trimethylammonium chloride (a/k/a chlorohydrin (commercially available from Quab Chemicals Inc. as a 65% aqueous solution under the name QUAB 188)).
A particularly preferred quaternary ammonium compound is glycidyltrimethylammonium chloride or its equivalent.

The derivatization reaction with the quaternary ammonium compound can be carried out in a single step or as two or more steps with or without intermediate separation and purification of the product. In the single step or two or more steps, the reaction is carried out by activating the polysaccharide with a base, preferably in water or other organic solvents, followed by reaction with the quaternary ammonium compound.

When the polysaccharide is reacted with the quaternary ammonium compound in a solvent-based medium, preferably the solvent is one that disperses or swells the polysaccharide. Suitable solvents include a mixture of water with aliphatic alcohols, in particular those having 1-4 carbon atoms; polyalcohols with 2-8 carbon atoms, in particular ethylene and diethylene glycol and glycerin; aliphatic ketones, in particular acetone; linear and cyclic ethers, in particular dioxane; and aliphatic and aromatic hydrocarbons with 6-15 carbon atoms. For cosmetic applications, the solvent must be cosmetically or dermatologically acceptable, and can comprise water and/or other organic solvents such as $C_1$-$C_4$ lower alcohols (e.g., ethanol, isopropanol, tert-butanol or n-butanol); alkylene polyols (e.g., propylene glycol); polyol ethers; and mixtures thereof.

Typically, the quaternary ammonium compound is used in excess, for example, in a molar ratio based on saccharide units in the polysaccharide of about 1:16 to about 1:2, more particularly about 1:12 to about 1:4. Where the derivatization reaction is carried out in two or more steps, a molar ratio of about 1:24 to about 1:8 preferably applies in each step. The base, preferably sodium hydroxide, is used in each step in a molar ratio of about 1:140 to about 1:25 based on hydroxyl groups in the monosaccharide units and in a molar ratio of about 2:1 to about 1:25, preferably about 1:2 to about 1:12, based on the quaternary ammonium compound when this is a compound according to formula (I), or about 1:2 to about 1:10 when this is a compound according to formula (II). The reaction temperature for each step may be from about 15° C. to about 120° C., preferably about 50° C. to about 100° C., and the reaction time overall may be, for example, about 1 to about 20 hours. When the derivatization reaction is carried out in two or more stages, the reaction time for each stage is generally about 0.25 to about 5 hours, preferably about 0.25 to about 3.5 hours.

The product may be neutralized by treatment with aqueous or organic acid (e.g., hydrochloric acid or lactic acid). The derivatized product can be isolated and purified by removing excess salts and residuals by washing, for example, with water or a mixture of water and solvent. The product is then recovered by filtration and/or centrifugation, and subsequently dehydrated, for example, by thermal drying. Acetone can optionally be used to remove at least some water and expedite drying.

Derivatized polysaccharides prepared as described above wherein one or more of $R^1$, $R^2$ and $R^3$ is hydrogen can subsequently be converted by an N-alkylation reaction into the corresponding compounds in which one or more of $R^1$, $R^2$ and $R^3$ is a hydrocarbon group, for example, with a compound of formula $R^5$ Hal where $R^5$ is an optionally substituted hydrocarbon group such as alkyl, hydroxyalkyl or alkenyl, and Hal is halogen, more particularly fluorine, chlorine, bromine or iodine, to effect quaternization of some or all of the ammonium groups.

The following structures are illustrative of different types of cationically modified polysaccharides—

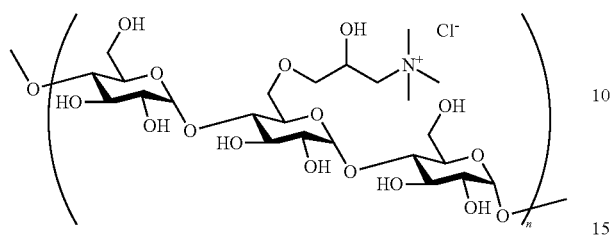

Illustrated above is the chemical structure of starch (amylose molecule) cationically modified with glycidyltrimethylammonium chloride.

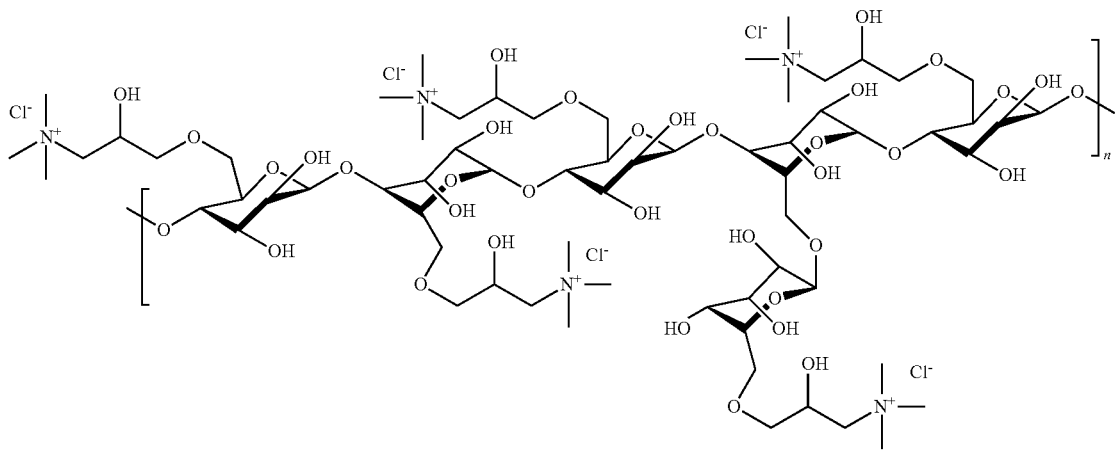

The above chemical structure is that of the cassia polymer cationically modified with glycidyltrimethylammonium chloride (3.0 mEq/g).

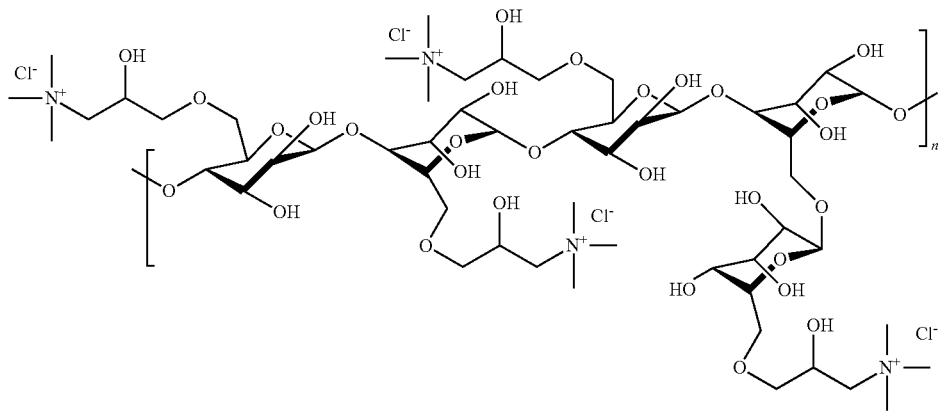

Illustrated above is the chemical structure of the locust bean polymer cationically modified with glycidyltrimethylammonium chloride (3.0 mEq/g).

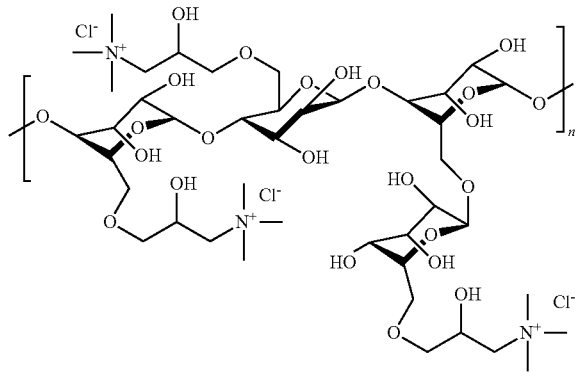

Illustrated above is the chemical structure of the tars polymer cationically modified with glycidyltrimethylammonium chloride (3.0 mEq/g).

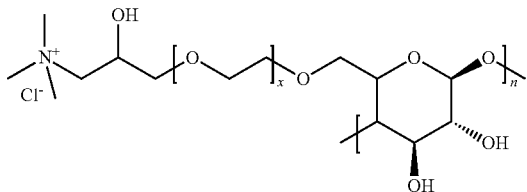

Illustrated above is the chemical structure of Polyquaternium-10 (PQ-10) (cationically modified hydroxyethyl cellulose (HEC) (cationically modified with glycidyltrimethylammonium chloride)).

Cationically modified polysaccharides according to the present invention generally have a charge density of about 0.1 to about 2.5 meq/g; more preferably, about 0.2 to about 2.0 meq/g; and even more preferably, about 0.8 to about 1.5 meq/g. As used herein, the "charge density" of the cationically modified polysaccharide refers to the ratio of the number of positive charges on the polysaccharide to the molecular weight of that polysaccharide.

When the polysaccharide is a gum, the gum has a weight average molecular weight ($MW_w$) of about 50,000 to about 10,000,000 g/mol prior to any degradation.

Monomeric silicon compounds are known as silanes. Silanes can vary in their chemistry, as illustrated in the following silane structure—

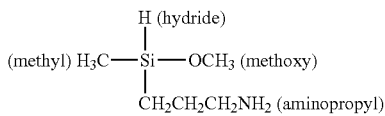

The above substituents are examples of different types of compounds that can bind with silicon. A silane that contains at least one carbon-silicon bond (e.g., $H_3C$—Si—) is known as an organosilane. When the other three substituents of the organosilane are all highly reactive hydride, these hydrides can react with water (e.g., by condensation reaction) to yield reactive silanol (—Si—OH) species as illustrated by the following structure—

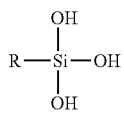

Siliconates include organosiliconates such as alkyl siliconates and phenyl siliconates and salts thereof. Salts include sodium and potassium salts. Alkali metal alkyl siliconates include those defined by the general formula:

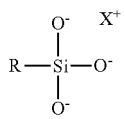

wherein R is an alkyl group containing 1 or more carbons (e.g., methyl, ethyl, propyl, phenyl), and X is an alkali metal (e.g., $Na^+$ or $K^+$). For example, when the alkali metal alkyl siliconate is sodium methyl siliconate, R is methyl and X is sodium. Exemplary species of alkali metal organosiliconates include sodium methylsiliconate, sodium ethylsiliconate, sodium propylsiliconate, potassium methylsiliconate, potassium ethylsiliconate and potassium propylsiliconate.

Sodium or potassium salts of methyl siliconate are commercially available as, for example, XIAMETER® OFS-0772 Siliconate (sodium salt) or XIAMETER® OFS-0777 Siliconate (potassium salt) (both available from Dow Corning). For the sodium methyl siliconate product XIAMETER® OFS-0772, the structure above can be illustrated with two hydroxyl functional groups (—OH) and the third oxygen ionized to OX, where X is sodium.

As indicated above, the polysaccharide can optionally be cross-linked either in the same reaction as the derivatization reaction or preferably subsequently thereto. Suitable cross-linking agents for polysaccharides include:
formaldehyde;
methylolated nitrogen compounds such as dimethylolurea dimethylolethyleneurea and dimethylolimidazolidone;
diacarboxylic acids such a maleic acid;
dialdehydes such as glyoxal;
diepoxides such as 1,2:3,4-diepoxybutane and 1,2:5,6-diepoxyhexane;
diisocyanates;
divinyl compounds such as divinylsulphone;
dihalogen compounds such as dichloroacetone, dichloroacetic acid, 1,3-dichloropropan-2-ol, dichloroethane, 2,3-dibromo-1-propanol, 2,3-dichloro-1-propanol and 2,2-dichloroethyl ether;
halohydrins such as epichlorohydrin;
bis(epoxypropyl)ether;
vinylcyclohexenedioxide;
ethylene glycol-bis(epoxypropyl)ether;
1,3-bis(β-hydroxy-Γ-chloropropoxy)-2-propanol;
1,3-bis(β-hydroxy-Γ-chloropropoxy)ethane;
methylenebis(acrylamide);
N,N'-dimethylol(methylenebis(acrylamide));
triacrylolhexahydrotriazine;
acrylamidomethylene chloroacetamide;
phosphates such as phosphorus oxychloride;
2,4,6-trichloropyrimidine;
2,4,5,6-tetrachloropyrimidine cyanuric chloride;
triallylcyanurate phosphorusoxychloride; and
bis(acrylamido)acetic acid.

Preferred cross-linking agents include di-epoxy compounds and haloepoxy compounds such as 1,3-bis(glycidyldimethylammonium)propanedichloride and epichlorohydrin; more preferably phosphate compounds, particularly phosphorus oxychloride ($POCl_3$).

When the cross-linking and derivatization reactions are carried out together, the conditions are as described above for the derivatization reaction. When the cross-linking reaction is carried out as a subsequent step following the derivatization reaction, the reaction conditions are also generally as described above for the derivatization reaction. The amount of cross-linking agent required will depend on the nature of the agent, the starting material and the conditions of the cross-linking reaction. In all cases the reaction should be such as to provide a degree of cross-linking which imparts the desired water insolubility to the polymer but does not interfere with the water absorption properties of the polymer (superabsorbent properties) imparted by the quaternary ammonium group.

Preferably, the cross-linking reaction is carried out at a temperature of about 15° C. to about 110° C., more preferably about 35° C. to about 85° C. for a time of about 1 to about 20 hours, preferably about 2 to about 10 hours.

The degree of substitution and the degree of cross-linking can both be controlled by appropriate variation in the amounts of starting materials and the reaction conditions, in particular, the concentration of the derivatizing and/or cross-linking reagent, reaction time, amount of base, reaction temperature, and the nature of the substrate. Depending upon the type of polysaccharide (e.g., cellulose, starch, polygalactomannan), appropriate modifications will need to be made to the reaction conditions (e.g., it is known that starch is generally more reactive than cellulose).

The process as described above leads to the polysaccharide derivative with deprotonated hydroxyl groups as a result of the use of base (e.g., NaOH) as a catalyst in the derivatization and cross-linking reactions. In general the polysaccharide is required in neutralized form and this can be prepared by treatment with acid (e.g., HCl, acetic acid or lactic acid) to neutral pH, or optionally neutralized by washing with water to neutral pH. If necessary, the polysaccharide in its neutral form can be deprotonated by treatment with strong base (e.g., NaOH), optionally followed by washing with water.

Modified polysaccharides according to the present invention are useful in a variety of detergent or rinse-off applications, including industrial cleaners, household detergents and personal care compositions such as shampoos and body washes, as well as leave-on applications such as car or wood polishes. In general, the formulations include one or more surfactants, the modified polysaccharide, and a carrier, as well as other ingredients depending upon the formulation's particular application.

In one aspect, modified polysaccharides according to the present invention are useful in personal care compositions, including conditioners and conditioning shampoos. Such personal care compositions comprise, in a cosmetically acceptable medium, a modified polysaccharide having both cationic and silicon constituents as described above, preferably in an amount ranging from about 0.1% to about 3.0% by weight relative to the total weight of the composition (w/w), with concentrations of from about 0.20% w/w to about 2.0% w/w being more preferred, even more preferably from about 0.25% w/w to about 1.5% w/w.

The term "cosmetically acceptable medium" refers to a medium that is compatible with at least one keratin material (e.g., skin, hair, nails, eyelashes, eyebrows, lips and any other area of body or facial skin). Such cosmetically acceptable medium can consists solely of water, or a mixture of water and a cosmetically acceptable solvent such as a $C_1$-$C_4$ lower alcohol (e.g., ethanol, isopropanol, tert-butanol or n-butanol); alkylene polyols (e.g., propylene glycol); polyol ethers; and mixtures thereof.

Personal care compositions according to the invention include those of the "rinse-off" category. These include, for example, shampoos, rinse-off conditioners, body washes, facial washes, liquid and bar soaps, hydro-alcoholic based products such as hand sanitizers and so forth which can be readily washed off with water. Personal care compositions according to the invention include those of the "leave-on" category, such as sunscreens, lotions, combing creams, insect repellants and so forth which are intended to remain on the skin or hair for an extended period. Additional leave-ons include color cosmetics such as pigmented skin colorants, nail polish and nail polish remover, mascara, rouge, lipstick and balm.

The composition according to the invention can also comprise one or more standard additives well known in the art, such as anionic, cationic, nonionic, amphoteric or zwitterionic surfactants; anionic, cationic, nonionic, amphoteric or zwitterionic polymers; thickeners; nacreous agents; opacifiers; UV-screening agents; fragrances; mineral, plant and/or synthetic oils; fatty acid esters; dyes; mineral or organic, natural or synthetic particles; preserving agents; and pH stabilizers. Surfactants can be present in the composition in an amount from about 5 wt % to about 60 wt % by weight of the composition. Other optional additives are generally present in the composition according to the invention in an amount ranging from about 0 to about 20% by weight, based on total weight of the composition. One skilled in the art will select these optional additives and their amount in a manner such that they do not harm the properties of the compositions of the present invention.

Anionic surfactants useful in the surface modifying compositions include ammonium lauryl sulfate, ammonium laureth sulfate, triethylamine lauryl sulfate, monoethanolamine lauryl sulfate, monoethanolamine laureth sulfate, diethanolamine lauryl sulfate, diethanolamine laureth sulfate, triethylamine laureth sulfate, triethanolamine lauryl sulfate, triethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocyl sulfate, ammonium lauroyl sulfate, sodium cocoyl sulfate, sodium lauroyl sulfate, potassium cocoyl sulfate, potassium lauroyl sulfate, monoethanolamine cocoyl sulfate, and combinations thereof.

Other suitable anionic surfactants include the reaction product of fatty acids esterified with isethionic acid and neutralized with sodium hydroxide where the fatty acids are derived from, for example, coconut oil or palm kernel oil, and sodium or potassium salts of fatty acid amides of methyl tauride.

Still other anionic surfactants suitable for use in the surface modifying compositions include various succinnates, examples of which include disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, diamyl esters of sodium sulfosuccinic acid, dihexyl esters of sodium sulfosuccinic acid, and dioctyl esters of sodium sulfosuccinic acid.

Other suitable anionic surfactants also include olefin sulfonates having about 10 to about 24 carbon atoms. Olefin sulfonates refer to those compounds that can be produce by sulfonation of α-olefins using uncomplexed sulfur trioxide, followed by neutralization of the acid reaction mixture under conditions such that any sulfones formed in the reaction are hydrolyzed to give the corresponding hydroxy-alkanesulfonates. The α-olefins from which the olefin sulfonates are derived are preferably mono-olefins having from about 10 to about 24 carbon atoms, preferably from about 12 to about 16 carbon atoms. Preferably, they are straight chain olefins.

Another class of anionic surfactants suitable for use herein are f-alkyloxy alkane sulfonates. Such surfactants conform to the following formula—

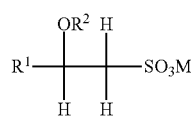

where $R^1$ is a straight chain alkyl group having from about 6 to about 20 carbon atoms; $R^2$ is a lower alkyl group having from about 1 to about 3 carbon atoms, preferably 1 carbon atom; and M is a water-soluble cation.

In addition to the sulfates, isethinoates, sulfonates and sulfosuccinates described above, other potential anions for the anionic surfactant include phosphonates, phosphates and carboxylates.

Surface modifying compositions according to the present invention can also include one or more additional surfactants such as amphoteric surfactants, zwitteronic surfactants, cationic surfactants and nonionic surfactants. Suitable amphoteric, zwitteronic, cationic and nonionic surfactants for use herein include those known for use in hair care or other personal care compositions (e.g., cocamidopropyl betaine and/or lauramidopropyl betaine). The concentration of such surfactants preferably ranges from about 0.5% to about 20.0% w/w, preferably from about 1.0% to about 10.0% by weight of the composition.

The surfactants are preferably present in the surface modifying compositions at concentrations of about 35% or less, more preferably about 20% or less, and even more preferably about 15% or less by weight of the composition.

Other optional ingredients include compounds and ingredients that modify the aesthetics of the final composition. For example, fragrances and natural oils can be used to provide a desirable odor, while dyes, pigments, opacifying or pearlescent agents can be used to impart a more appealing appearance. From a performance perspective, vitamins, amino acids and humectants can provide enhanced protective and reparative functionality. Of particular use are ingredients that protect, prolong or enhance the intensity of hair colorants or skin and nail coloring compositions.

Non-detersive conditioning agents useful in the practice of the invention can be selected from a variety of categories. Particularly useful conditioning agents include oily substances, waxes, nonionic substances, cationic ingredients, amphiphilic ingredients, cationic polymers and mixtures thereof. Oily substances include natural oils (e.g., olive oil, almond oil, wheat germ oil, ricinus oil) and synthetic oils (e.g., mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Moisturizing agents such as panthenols and polyols (e.g., glycerol, polyethylene glycols having a molecular weight from about 200 to about 20,000) can also be present as non-detersive conditioning agents. The moisturizing ingredients can be present in the compositions at a concentration of about 0.01 to about 2.5% by weight of the total composition. Additional moisturizing agents include ester-based emollients such as cetyl lactate, lauryl lactate, $C_{12}$ to $C_{15}$ lactate, dicetyl malate, myristyl lactate, decyl oleate, isodecyl oleate, diisopropyl adipate, isocetyl alcohol, isodecyl neopentanoate, ethylhexyl palmitate, isocetyl stearate, myristyl myristate and myristyl laurate, glycidyl dilaurate, tridecyl neopentanoate, isostearyl neopentanoate, octyldodecyl stearate, isocetyl stearoyl stearate, octyldodecyl stearoyl stearate, and carpylic/capric triglyceride.

Nonionic conditioning agents can be present in the composition in a range of from about 0.01% to about 10.00% by weight of the total composition, preferably about 0.05% to about 7.50%, more preferably about 0.10% to about 5.00%, and most preferably about 0.10% to about 3.00% by weight of the total composition.

Other cationic ingredients can also be used as non-detersive conditioning agents such as cetyltrimethyl ammonium chloride, steartrimonium chloride, behentrimonium chloride, stearamidopropyl trimonuim chloride, dioleoylethyl dimethyl ammonium methosulfate, and dioleoylethyl hydroxyethylmonium methosulfate. Amido amines such as stearamidopropyl dimethyl amine can also be used as a conditioning cationic surfactant in compositions of the present invention.

Other suitable conditioning ingredients include glyceryl ethers such as glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, glyceryl myristyl ether, glyceryl palmityl ether, glyceryl stearyl ether and glyceryl behenyl ether and their mixtures. Most preferred are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether are glyceryl lauryl ether, and the like.

Still other non-detersive conditioning ingredients include polyphenols such as those derived from aqueous and alcoholic plant extracts. Suitable extracts include those derived from aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn and the like.

Personal care formulations according to the present invention can also contain other ingredients for improving their appearance and consumer appeal such as fragrances, dyes, colorants, pigments, bleaches, pearlescent agents (e.g., mica and titanium dioxide coated mica), opacifying agents and the like. Rheology modifiers such as carbomer, poly(vinylpyrrolidone), hydroxypropyl methylcellulose, hydroxypropyl cellulose, sodium polyacrylates can be employed to provide thickening or other aesthetically-pleasing characteristics.

For a more detailed understanding of the invention, reference can be made to the following examples, which are intended as further illustrations of the invention but are not to be construed in a limiting sense. All parts and percentages are by weight unless stated otherwise.

EXAMPLES

Example 1—Modified Polysaccharide Preparation—

Various samples of modified tara gum were prepared having different amounts of cationization as well as different amounts of silicon constituents for comparison. An additional comparative sample was prepared having only cationic modification.

The method of preparing the modified polysaccharide samples was as follows. An aqueous solution of isopropanol, NaOH and tara gum was mixed together with stirring at 60° C. Glycidyltrimethylammonium chloride was added to the solution and allowed to react with the tara gum for 3 hours at 60° C. The cationically modified mixture was then cooled to 40° C. After cooling to 40° C., the cationically modified gums were reacted with sodium methylsiliconate (with the exception of comparative Example 5, to which no silicone modification was performed) in the amount indicated in the above Table for 1 hour, followed by neutralization of the modified gums with HCl, then filtration, and subsequent washing with 80% isopropanol. The samples were then dried overnight at 40° C. The formulae used in forming the modified polysaccharides are provided in the following Table:

TABLE 1

Modified Polysaccharide Formulae

| Ingredient (wt %)[1] | Sample ID | | | | |
|---|---|---|---|---|---|
| | 1 | 2 | 3 | 4 | 5 (comparative) |
| Tara gum | 100% | 100% | 100% | 100% | 100% |
| Isopropanol (90%) | 167% | 167% | 167% | 167% | 167% |
| NaOH (25%)[2] | 12% | 12% | 12% | 12% | 12% |
| glycidyltrimethyl-ammonium chloride[3] | 18% | 18% | 18% | 28% | 18% |
| sodium methylsiliconate[4] | 6% | 12% | 24% | 24% | 0% |
| HCl (3M)[5] | 28-47% | 28-47% | 28-47% | 28-47% | 28-47% |
| Isopropanol (80%) | 400% | 400% | 400% | 400% | 400% |

[1] Wt % is relative to 100% polysaccharide used.
[2] 12% based on aqueous 25% NaOH weight (anhydrous NaOH weight would be 3%).
[3] QUAB ® 151 (glycidyltrimethylammonium chloride), commercially available from SKW Quab Chemicals Inc., Saddle Brook, New Jersey USA.
[4] XIAMETER ® OFS-0772 Siliconate (sodium methyl siliconate), commercially available from Dow Chemical, Midland, Michigan USA.
[5] Targeted pH for the neutralization step is in the range of 4 to 7. Hence, the amount of 3M HCl required to neutralize this product is presented as a range.

Dried modified tam gum was analyzed in radial mode using a Thermo Scientific™ iCAP™ 7000 Series ICP-OES (Inductively Coupled Plasma-Optical Emission Spectroscopy) at silicon wavelength 221.667 nm in order to determine the amount of silicon bonded to the gum. The results are provided in Table 2 below—

TABLE 2

Silicon Bound to Polysaccharide

| Sample ID | Silicon[1] Treatment (%) | Cationic[2] Treatment (%) | Si (ppm) |
|---|---|---|---|
| 1 | 6 | 18 | 782 ± 5.56 |
| 2 | 12 | 18 | 1919 ± 26.12 |
| 3 | 24 | 18 | 2915 ± 71.16 |
| 4 | 24 | 28 | 1782 ± 43.16 |
| 5 | 0 | 18 | Below Detection Limit |

[1] XIAMETER ® OFS-0772 Siliconate (sodium methyl siliconate), commercially available from Dow Chemical, Midland, Michigan USA.
[2] QUAB ® 151 (glycidyltrimethylammonium chloride), commercially available from SKW Quab Chemicals, Inc., Saddle Brook, New Jersey USA.

The above results illustrate firstly incorporation of silicon into a cationic tara gum backbone. As the amount of silicon (XIAMETER® OFS-0772) level increases (from 6 to 24%, Samples 1 through 3) the amount of bound silicon increases. Secondly, it is seen that an increased degree of tara gum quaternization results in a lower degree of siliconation (sample 4). This phenomenon can be possibly explained by the reduced amount of available binding sites for the silicon (XIAMETER® OFS-0772) and/or increased steric hindrance that inhibits silicon access to the cationic tara gum backbone. Therefore, careful adjustment of both substituents is required to obtain maximum performance in both deposition (via quaternization) and sensory benefits (via siliconation).

Example 2—Shampoo Formulation—

Conditioning properties of a standard shampoo composition containing various modified polysaccharides were evaluated. All testing was performed on hair procured from International Hair Importers & Products (Glendale, N.Y.). Hair tresses weighed approximately 3 g and measured 8 inches (20.32 cm) in length and 1 inch (2.54 cm) in width. Prior to testing, the tresses were bleached using a 6% hydrogen peroxide at a pH of 10.2. The tresses were left in contact with the bleach solution for 40 minutes under controlled temperature conditions (40° C.). At the end of this process, tresses were thoroughly rinsed under an Intellifaucet rinsing apparatus set at 40° C. with a controlled flow rate of 1.0 GPM. Various shampoo formulations with and without modified polysaccharides were produced and tested according to the following formulations—

TABLE 3

Shampoo Formulations

| Basic Shampoo Ingredients | Control 1[1] (wt %) | Control 2[2] (wt %) | Shampoo 1 (wt %) | Shampoo 2 (wt %) |
|---|---|---|---|---|
| Deionized water | 53.95 | 52.31 | 54.15 | 54.15 |
| Sample 1[3] | — | — | 0.25 | — |
| Sample 2 | — | — | — | 0.25 |
| Polyquaternium-10[4] | 0.25 | 0.25 | — | — |
| Polydimethylsiloxane[5] | — | 1.64 | — | — |
| Surfactant blend[6] | 44.00 | 44.00 | 44.00 | 44.00 |
| Lactic Acid[7] | 1.30 | 1.30 | 1.10 | 1.10 |
| Preservative[8] | 0.50 | 0.50 | 0.50 | 0.50 |
| Total | 100.00 | 100.00 | 100.00 | 100.00 |

[1] Control 1 is a shampoo formulation having only cationic charge (Polyquaternium-10) and no modified polysaccharide according to the invention.
[2] Control 2 (comparative) is a shampoo formulation having both cationic charge (Polyquaternium-10) and addition of silicon as a separate ingredient but no modified polysaccharide according to the invention.
[3] See Table 1 above for Sample 1 and Sample 2
[4] UCARE ™ Polymer JR-30M, available from The Dow Chemical Company, Midland Michigan USA.

TABLE 3-continued

Shampoo Formulations

| Basic Shampoo Ingredients | Control 1 [1] (wt %) | Control 2 [2] (wt %) | Shampoo 1 (wt %) | Shampoo 2 (wt %) |
|---|---|---|---|---|

[5] XIAMETER ® MEM-1785 Emulsion (INCI: Dimethiconol (and) TEA-Dodecylbenzenesulfonate), available from Dow Corning, Midland, Michigan USA.
[6] Miracare ® Plaisant (INCI: Aqua (and) Sodium Cocoyl Isethionate (and) Sodium Lauroamphoacetate (and) Sodium Methyl Cocoyl Taurate), available from Solvay Novecare, Princeton, New Jersey USA.
[7] PURAC ® HiPure 90, available from Corbion, Amsterdam, The Netherlands.
[8] Microcare ® PHI (INCI: Phenoxyethanol (and) Iodopropynyl Butylcarbamate), available from Thor Personal Care SAS, La Croix Saint-Ouen, France.

All product treatments were conducted according to the following procedure. Shampoo was applied at a quantity of 0.1 g/g of hair of shampoo applied to tress of wet hair and massaged in between thumb and forefinger for thirty (30) seconds. The tress was then rinsed under Intellifaucet rinsing apparatus set at 38° C. and 1 gal/min for 30 seconds.

Shampoo Results—

The primary technical function of most conditioning products is to lubricate the hair surface and, in doing so, facilitate manageability and provide detangling benefits and lower combing friction. Comparative results of shampoo formulations containing modified polysaccharides according to the invention against control formulations are shown in the following Tables. Results are based on testing using five (5) panelists and presented as the average of the score cards from 1 to 5, with 5 being the best. Positive results for the modified polysaccharide formulations should show those formulations to be comparative to or better than formulations containing PQ-10 and silicon separately (Control 2 Shampoo above).

TABLE 4

Wet Feel Results (Panelists Averaged Score card)
(Shampoos were formulated according to the recipe described in Table 3)

| Control 3 [1] | Control 4 [4] | Shampoo 1 | Control 2 Shampoo |
|---|---|---|---|
| 1 | 5 | 3 | 4 |
| 1 | 5 | 4 | 4 |
| 2 | 4 | 3 | 3 |
| 2 | 4 | 2 | 3 |
| 1 | 5 | 3 | 4 |
| Total Score: 7 | Total Score: 23 | Total Score: 15 | Total Score: 18 |

[1] Control 3 represents a negative control (a 15% SLES only (surfactant only)) solution; i.e., the hair tresses were washed using only a surfactant solution and evaluated.
[2] Control 4 represent commercial shampoo (Dove Daily Moisture Shampoo & Conditioner) comparative; i.e., the hair tresses were washed using the commercial shampoo and evaluated.

TABLE 5

Wet Comb Results (Panelists Averaged Score card)
(Shampoos were formulated according to the recipe described in Table 3)

| Control 3 | Control 4 | Shampoo 1 | Control 2 |
|---|---|---|---|
| 1 | 5 | 3 | 4 |
| 1 | 5 | 3 | 4 |
| 1 | 5 | 4 | 3 |

TABLE 5-continued

Wet Comb Results (Panelists Averaged Score card)
(Shampoos were formulated according to the recipe described in Table 3)

| Control 3 | Control 4 | Shampoo 1 | Control 2 |
|---|---|---|---|
| 1 | 5 | 2 | 4 |
| 1 | 5 | 4 | 4 |
| Total Score: 5 | Total Score: 25 | Total Score: 16 | Total Score: 19 |

TABLE 6

Dry Feel Results (Panelists Averaged Score card)
(Shampoos were formulated according to the recipe described in Table 3)

| Control 3 | Control 4 | Shampoo 1 | Control 2 |
|---|---|---|---|
| 3 | 5 | 5 | 4 |
| 3 | 5 | 5 | 5 |
| 4 | 5 | 5 | 4 |
| 3 | 5 | 5 | 4 |
| 4 | 5 | 4 | 4 |
| Total Score: 17 | Total Score: 25 | Total Score: 24 | Total Score: 21 |

TABLE 7

Results from Dry Comb (Panelists Averaged Score card)
(Shampoos were formulated according to the recipe described in Table 3)

| Control 3 | Control 4 | Shampoo1 | Control 2 |
|---|---|---|---|
| 3 | 5 | 4 | 4 |
| 3 | 5 | 3 | 4 |
| 4 | 5 | 4 | 5 |
| 3 | 5 | 5 | 4 |
| 3 | 5 | 4 | 5 |
| Total Score: 16 | Total Score: 25 | Total Score: 20 | Total Score: 22 |

The results show that the formulations of the invention (Sample 1 modified polysaccharide with 18% cationization and 6% silicon—Shampoo 1) are equivalent to or better than the Control 2 Shampoo having both PQ10 and silicon as separate ingredients.

As will be appreciated by one skilled in the art, the invention provides a wide variety of industrial, home care and personal care surface modifying formulations. For example, the invention provides a wide variety of cosmetic and dermatologically acceptable personal care formulations as exemplified below. Those of ordinary skill in the art will appreciate that these formulations can be modified, and that other personal care formulations can be produced using the modified polysaccharides described herein.

Example of formulations in which the modified polysaccharide can be used are as follows—

TABLE 8

Shampoo with no Silicone

| Ingredient | Wt % |
|---|---|
| Deionized water | 74.88 |
| Modified polysaccharide[1] | 0.50 |
| Sodium Laureth Sulfate[2] | 12.85 |
| Cocamidopropyl Betaine[3] | 8.57 |
| Sodium Chloride | 1.00 |
| Fragrance (Parfum) | 0.60 |
| Disodium EDTA[4] | 0.10 |

TABLE 8-continued

Shampoo with no Silicone

| Ingredient | Wt % |
|---|---|
| Lactic acid[5] | 1.00 |
| Preservative[6] | 0.50 |
| Total | 100.00 |

[1]Modified polysaccharide according to the invention (e.g., Sample 1 or Sample 2 above).
[2]TEXAPON ® N 70 NA anionic surfactant, available from BASF Corporation, Florham Park, New Jersey USA.
[3]AMPHOSOL ® CG amphoteric surfactant, available from Stepan Company, Northfield, Illinois USA.
[4]Edeta ® BD amino-carboxylic acid, available from BASF Corporation, Florham Park, New Jersey USA.
[5]PURAC ® HiPure 90, available from Corbion, Amsterdam, The Netherlands.
[6]Microare ® PHI (INCI: Phenoxyethanol (and) Iodopropynyl Butylcarbamate), available from Thor Personal Care SAS, LaCroix Saint-Ouen, France.

TABLE 9

Rinse-Off Conditioner

| Ingredient | Wt % |
|---|---|
| Deionized water | 87.25 |
| Modified polysaccharide[1] | 0.50 |
| Disodium EDTA[2] | 0.10 |
| Emulsifier[3] | 2.00 |
| Alcohol[4] | 2.00 |
| Alcohol[5] | 4.00 |
| Silicone[6] | 0.50 |
| Silicone[7] | 2.00 |
| Fragrance (Parfum) | 0.5 |
| Lactic acid[8] | 0.65 |
| Preservative[9] | 0.50 |
| Total | 100.00 |

[1]Modified polysaccharide according to the invention (e.g., Sample 1 or Sample 2 above).
[2]Edete ® BD amino-carboxylic acid, available from BASF Corporation, Florham Park, New Jersey USA.
[3]Lexamine ® S-13 wax emulsifier (INCI: Stearamidopropyl Dimethylamine), available from Inolex, Philadelphia, Pennsylvania USA.
[4]Lanette ® 16 viscosifier (INCI: Cetyl Alcohol), available from BASF Corporation, Florham Park, New Jersey USA.
[5]Lanette ® 18 viscosifier (INCI: Stearyl Alcohol), available from BASF Corporation, Florham Park, New Jersey USA.
[6]XIAMETER ® PMX-200 silicone fluid (INCI: Dimethicone), available from Dow Corning, Midland, Michigan USA.
[7]XIAMETER ® PMX-0345 cyclosiloxane blend (INCI: Cyclopentasiloxane (and) Cyclohexasiloxane), available from Dow Corning, Midland, Michigan USA.
[8]PURAC ® HiPure 90, available from Corbion, Amsterdam, The Netherlands.
[9]Microare ® SBB, liquid blend of benzyl alcohol, benzoic acid and sorbic acid, available from Thor Personal Care SAS, La Croix Saint-Ouen, France.

TABLE 10

Leave-In Moisturizer

| Ingredient | Wt % |
|---|---|
| Deionized water | 95.60 |
| Modified polysaccharide[1] | 0.35 |
| Silicon fluid[2] | 1.00 |
| Silicon emulsion[3] | 1.50 |
| Fragrance (Parfum) | 0.40 |
| Nonionic surfactant[4] | 0.40 |
| Lactic acid[5] | 0.25 |
| Preservative[6] | 0.50 |
| Total | 100.00 |

[1]Modified polysaccharide according to the invention (e.g., Sample 1 or Sample 2 above).
[2]XIAMETER ® OFX-0193 silicone fluid (INCI: PEG-12 Dimethicone), available from Dow Corning, Midland, Michigan USA.
[3]XIAMETER ® MEM-0949 cationic silicon polymer emulsion (INCI: Amodimethicone (and) Cetrimonium Chloride (and) Trideceth-12), available from Dow Corning, Midland, Michigan USA.
[4]Brij ® O20 (INCI: Oleth-20), available from Croda International Plc, East Yorkshire, England.
[5]PURAC ® HiPure 90, available from Corbion, Amsterdam, The Netherlands.
[6]Microare ® SBB, liquid blend of benzyl alcohol, benzoic acid and sorbic acid, available from Thor Personal Care SAS, La Croix Saint-Ouen, France.

TABLE 11

Hair Oil Moisturizer

| Ingredient | % |
|---|---|
| Deionized water | 87.90 |
| Modified polysaccharide[1] | 0.50 |
| Propylene glycol | 2.00 |
| Coconut oil[2] | 4.00 |
| Sunflower oil[3] | 4.00 |
| Fragrance (Parfum) | 0.60 |
| Lactic acid[4] | 0.50 |
| Preservative[5] | 0.50 |
| Salcare SC 96[6] | 2.50 |
| Total | 100.00 |

[1]Modified polysaccharide according to the invention (e.g., Sample 1 or Sample 2 above).
[2]Rita Coconut Oil 76 (INCI: Cocos Nucifera (Coconut) Oil), available from RITA Corporation, Crystal Lake, Illinois USA.
[3]Florasun ® 90 sunflower oil (INCI: Helianthus Annus (Sunflower) Seed Oil), available from FloraTech, Chandler, Arizona USA.
[4]PURAC ® HiPure 90, available from Corbion, Amsterdam, The Netherlands.
[5]Microare ® SBB, liquid blend of benzyl alcohol, benzoic acid and sorbic acid, available from Thor Personal Care SAS, La Croix Saint-Ouen, France.
[6]Salcare ® SC 96 cationic homopolymer moisturizer (INCI: Polyquaternium-37, Propylene Glycol Dicaprylate/Dicaprate, PPG-1 Trideceth-6), available from BASF Corporation, Florham Park, New Jersey USA.

TABLE 12

Sulfate-Free Shampoo

| Ingredient | Wt % | Wt % | Wt % | Wt % |
|---|---|---|---|---|
| Deionized water | 69.95 | 86.90 | 69.95 | 86.90 |
| Sample 1[1] | 0.80 | | | 0.80 |
| Sample 2[1] | | 0.80 | 0.80 | |
| Amphoteric surfactant[2] | 16.67 | 10.00 | 16.67 | 10.00 |
| Anionic surfactant[3] | 11.28 | 1.00 | 11.28 | 1.00 |
| Chelating agent[4] | 0.10 | 0.10 | 0.10 | 0.10 |
| Fragrance (Parfum) | 0.60 | 0.60 | 0.60 | 0.60 |
| Lactic Acids[5] | 0.10 | 0.10 | 0.10 | 0.10 |
| Preservative[6] | 0.50 | 0.50 | 0.50 | 0.50 |
| Total | 100.00 | 100.00 | 100.00 | 100.00 |

[1]See Table 1 above.
[2]AMPHOSOL ® CBD SPECIAL (INCI: Cetyl Betaine), available from the Stepan Company, Northfield, Illinois USA.
[3]Hostapon ® SCI-85 C (INCI: Sodium Cocoyl Isethionate), available from Clariant International Ltd., Muttenz, Switzerland.
[4]EDETA ® BX Powder (INCI: Tetrasodium EDTA), available from BASF, Ludwigshafen, Germany.
[5]PURAC ® HiPure 90, available from Corbion, Amsterdam, The Netherlands.
[6]Microare ® SBB, liquid blend of benzyl alcohol, benzoic acid and sorbic acid, available from Thor Personal Care SAS, La Croix Saint-Ouen, France.

TABLE 13

Sulfate-Free Body Wash

| Ingredient | Wt % |
|---|---|
| DI Water | 65.95 |
| Modified Polysaccharide[1] | 0.80 |
| Humectant[2] | 2.00 |
| Amphoteric surfactant[3] | 16.67 |
| Anionic surfactant[4] | 11.28 |
| Opacifier[5] | 1.50 |
| Chelating agent[6] | 0.10 |
| Fragrance (Parfum) | 0.60 |
| Lactic acid[7] | 0.10 |
| Preservative[8] | 1.00 |
| Total | 100.00 |

[1]Modified polysaccharide according to the invention (e.g., Sample 1 or Sample 2 above).
[2]Glystar ® A-31 (INCI: Hydrogenated Starch Hydrolysate), available from Ingredion Inc., Westchester, Illinois USA.
[3]AMPHOSOL ® CBD SPECIAL (INCI: Cetyl Betaine), available from the Stepan Company, Northfield, Illinois USA.
[4]Hostapon ® SCI-85 C (INCI: Sodium Cocoyl Isethionate), available from Clariant International Ltd., Mullenz, Switzerland.
[5]Cutina ® EGMS (INCI: Glycol Stearate), available from BASF Corporation, Florham Park, New Jersey USA.

TABLE 14

Body Wash

| Ingredient | wt % |
| --- | --- |
| DI Water | 42.99 |
| Modified Polysaccharide[1] | 0.60 |
| Humectant[2] | 2.00 |
| Amphoteric surfactant[3] | 14.29 |
| Anionic surfactant[4] | 36.67 |
| Opacifier[5] | 1.50 |
| Chelating agent[6] | 0.25 |
| Fragrance (Parfnin) | 0.60 |
| Lactic acid[7] | 0.10 |
| Ammonium Chloride | 0.50 |
| Preservative[8] | 0.50 |
| Total | 100.00 |

[1]Modified polysaccharide according to the invention (e.g., Sample 1 or Sample 2 above).
[2]Glystar ® A-31 (INCI: Hydrogenated Starch Hydrolysate), available from Ingredion Inc., Westchester, Illinois USA.
[3]AMPHOSOL ® HCG-HP (INCI: Cocamidopropyl Betaine), available from the Stepan Company, Northfield, Illinois USA,
[4]Calfoam ® ES-302 (INCI: Sodium Lauryl Ether Sulfate), available from Clariant International Ltd., Muttenz, Switzerland.
[5]Cutina ® EGMS (INCI: Glycol Stearate), available from BASF Corporation, Florham Park, New Jersey USA,
[6]EDETA ® BX Powder (INCI: Tetrasodium EDTA), available from BASF, Ludwigshafen, Germany.
[7]PURAC ® HiPure 90, available from Corbion, Amsterdam, The Netherlands.
[8]Microcare ® SBB, liquid blend of benzyl alcohol, benzoic acid and sorbic acid, available from Thor Personal Care SAS, La Croix Saint-Ouen, France.

TABLE 15

Styling Lotion

| Ingredient | Wt % |
| --- | --- |
| DI Water | 93.00 |
| Modified Polysaccharide[1] | 0.75 |
| Cationic Copolymer[2] | 3.00 |
| Moisturizer[3] | 0.50 |
| Lactic acid[4] | 0.25 |
| Preservative[5] | 1.00 |
| Fragrance (Parfum) | 0.50 |
| Nonionic surfactant[6] | 1.00 |
| Total | 100.00 |

[1]Modified polysaccharide according to the invention (e.g., Sample 1 or Sample 2 above).
[2]Gafquat ® 755N (INCI: Polyquatemium-11), available from Ashland Inc., Covington, Kentucky USA.
[3]Solulan ® 75 Lanolin Derivative (INCI: PEG-75 Lanolin), available from Lubrizol Advanced Materials, Cleveland, Ohio USA.
[4]PURAC ® HiPure 90, available from Corbion, Amsterdam, The Netherlands.
[5]Microcare ® SBB, liquid blend of benzyl alcohol, benzoic acid and sorbic acid, available from Thor Personal Care SAS, La Croix Saint-Ouen, France.
[6]Brij ® O20 (INCI: Oleth-20) (Chemical Descriptor: Polyoxyethylene (20) oleyl ether), available from Croda international PLC, Snaith, Goole, East Yorkshire, United Kingdom,

TABLE 16

Combing Cream

| Ingredient | Wt % |
| --- | --- |
| DI Water | 85.75 |
| Modified Polysaccharide[1] | 0.50 |
| Propylene Glycol | 2.00 |
| Fixative polymer[2] | 2.00 |
| Cetearyl Alcohol | 2.50 |
| Cationic Surfactant[3] | 2.00 |
| Silicone fluid[4] | 2.00 |
| Lactic acid[5] | 0.25 |
| Preservative[6] | 1.00 |
| Fragrance (Parfum) | 0.50 |
| Moisturizer[7] | 1.50 |
| Total | 100.00 |

[1]Modified polysaccharide according to the invention (e.g., Sample 1 or Sample 2 above).
[2]Styleze ® W-10 (INCI: Polyquaternium-55) (Chemical Descriptor: Vinylpyrrolidone/Dimethylamino propylmethacrylamide/Methacryloylaminopropyl Lauryl Dimethyl Ammonium Chloride Terpolymer), available from Ashland Inc., Covington, Kentucky USA.
[3]Genamin ® KDMP (INCI: Behentrimonium Chloride), available from Clariant, Muttenz, Switzerland.
[4]XIAMETER ® PMX-200 silicone fluid (INCI: Dimethicone), available from Dow Corning, Midland, Michigan USA.
[5]PURAC ® HiPure 90, available from Corbion, Amsterdam, The Netherlands.
[6]Microcare ® SBB, liquid blend of benzyl alcohol, benzoic acid and sorbic acid, available from Thor Personal Care SAS, La Croix Saint-Ouen, France.
[7]Salcare ® SC 96 cationic homopolymer moisturizer (INCI: Polyquaternium-37, Propylene Glycol Dicaprylate/Dicaprate, PPG-1 Trideceth-6), available from BASF Corporation, Florham Park, New Jersey USA.

TABLE 17

Moisturizing Lotion

| Ingredient | Wt % |
| --- | --- |
| DI Water | 79.51 |
| Modified polysaccharide[1] | 0.50 |
| Glycerin | 2.00 |
| Antimicrobial[2] | 0.10 |
| Emollient[3] | 3.00 |
| Nonionic surfactant[4] | 4.00 |
| Nonionic surfactant[5] | 4.00 |
| Shea butter[6] | 1.00 |
| Sunflower Oil[7] | 2.00 |
| Cocoa Butter[8] | 0.50 |
| 25% Sodium Hydroxide | 0.060 |
| Lactic acid[9] | 0.030 |
| Chelating agent[10] | 0.10 |
| Allantoin[11] | 0.25 |
| Humectant[12] | 1.00 |
| Silicon fluid[13] | 1.00 |
| Fragrance (Parfurn) | 0.75 |
| Nipaguard DMDMH[14] | 0.2 |
| Total | 100.00 |

[1]Modified polysaccharide according to the invention (e.g.. Sample 1 or Sample 2 above).
[2]Nipagin ® M Sodium (INCI: Sodium Methylparaben), available from Clariant, Muttenz, Switzerland.
[3]Ritamollient CCT (INCI: Caprylic/Capric Triglyceride), available from Rita Corporation, Crystal Lake, Illinois USA.
[4]Promulgen ™ D Nonionic Emulsifier (INCI: Cetearyl Alcohol (and) Ceteareth-20), available from Lubrizol Advanced Materials, Cleveland, Ohio USA.
[5]Promulgen ™ G Nonionic Emulsifier (INCI: Stearyl Alcohol (and) Ceteareth-20), available From Lubrizol Advanced Materials, Cleveland, Ohio USA.
[6]Shebu Refined (INCI: Butyrospermum Parkii (Shea Butter), available from Rita Corporation, Crystal Lake, Illinois USA.
[7]Rita SSO (INCI: Helianthus Annuus (Sunflower) Seed Oil), available from Rita Corporation, Crystal Lake, Illinois USA.
[8]Rita Cocoa Butter NF (INCI: Theobroma Cacao (Cocoa) Seed Butter), available from Rita Corporation, Crystal Lake, Illinois USA.
[9]PURAC ® HiPure 90, available from Corbion, Amsterdam, The Netherlands.
[10]EDETA ® BD (INCI: Disodium EDTA), available from BASF, Ludwigshafen, Germany.
[11]RonaCare ® Allantoin (INCI: AHantoin), available from Merck KGaA, Darmstadt, Germany.
[12]AJIDEW ® NL-50 UNCI: Sodium PC A (and) Aqua), available from Ajinomoto Co., Inc., Tokyo, Japan.
[13]XIAMETER ® PMX-200 silicone fluid (350 cps) (INCI: Dimethicone), available from Dow Corning, Midland, Michigan USA.
[14]Nipaguard ® DMDMH (INCI: DMDM Hydamoin), available from Clariant, Munenz, Switzerland.

TABLE 18

Hand Sanitizer

| Ingredient | Wt % |
| --- | --- |
| DI Water | 32.05 |
| Modified Polysaccharide[1] | 0.40 |
| Denatured alcohol | 62.00 |
| Glycerin | 5.00 |
| Chelating agent[2] | 0.05 |
| Fragrance (Parfum) | 0.50 |
| Total | 100.00 |

[1]Modified polysaccharide according to the invention (e.g., Sample 1 or Sample 2 above).
[2]EDETA ® BX Powder (INCI: Tetrasodium EDTA), available from BASF, Ludwigshafen, Germany.

The invention further provides a wide variety of industrial and home care formulations as exemplified below. Those of ordinary skill in the art will appreciate that these formulations can be modified, and that other formulations can be produced using the modified polysaccharides described herein.

Examples of industrial and home care formulations in which the modified polysaccharide can be used are as follows—

TABLE 19

Protective Coating for Automotive Painted Surface

| Ingredient | Wt % | Wt % |
| --- | --- | --- |
| Modified Polysaccharide[1] | 30-50 | 30-50 |
| Aminofunctional siloxane[2] | 15-20 | — |
| Alkylarylpolvsiloxane fluid[3] | — | 15-30 |
| Propylene glycol | 3-5 | |
| Detergent[4] | 52-25 | 52-25 |

[1]Modified polysaccharide according to the invention (e.g, Sample 1 or Sample 2 above).
[2]XIAMETER ® OFX-0536 Fluid (amino methoxy functional polydimethylsiloxane), available from available from Dow Corning, Midland, Michigan USA.
[3]XIAMETER ® OFX-0203 Fluid (100% active alkylaryl polysiloxane fluid), available from available from Dow Corning, Midland, Michigan USA.
[4]Dawn ® dishwashing liquid, available from The Procter & Gamble Company, Cincinnati, Ohio USA.

TABLE 20

Fabric Treatment Compositions

| INGREDIENTS (Wt %) | Formula 1 | Formula 2 | Formula 3 | Formula 4 |
| --- | --- | --- | --- | --- |
| Modified polysaccharide[1] | 6.81% | 7.48% | 9.00% | 11.9% |
| Nonionic surfactant[2] | 0.60% | 0.60% | 0.60% | 0.21% |
| Monopropylene glycol[3] | 0.00% | 3.45% | 3.88% | 1.81% |
| Glycerol | 5.00% | 5.00% | 5.00% | 0.77% |
| Perfume | 0.60% | 0.60% | 0.60% | 0.60% |
| Perfume microcapsule | 0.25% | 0.25% | 0.25% | 0.25% |
| Preservative | 0.0075% | 0.0075% | 0.0075% | 0.0075% |
| Structurant | 0.11% | 0.15% | 0.1% | 0.1% |
| Calcium chloride | 0.05% | 0.05% | 0.05% | 0.05% |
| Blue dye | 0.00028% | 0.00028% | 0.00028% | 0.00028% |
| Violet dye | 0.00052% | 0.00052% | 0.00052% | 0.00052% |
| Formic acid | 0.025% | 0.025% | 0.025% | 0.025% |
| Deionized water | Balance | Balance | Balance | Balance |

[1]Modified polysaccharide according to the invention (e.g., Sample 1 or Sample 2 above).
[2]CAE10 fatty acid ethoxylate (coconut fatty acid reacted with an average of ten moles of ethylene oxide).
[3]1,2-propanediol.
[4]Vitasyn ® Blue AE 90 dye, available from Clariant International Ltd, Muttenz, Switzerland.
[5]Sanolin ® Violet dye, available from Clariant International Ltd, Muttenz, Switzerland.

TABLE 21

Furniture Polish Compositions

| INGREDIENTS (Wt %) | Formula 1 | Formula 2 | Formula 3 | Formula 4 |
| --- | --- | --- | --- | --- |
| Modified polysaccharide[1] | 0.5% | 0.5% | 0.5% | 0.5% |
| Hydroxyacetic acid | 3.0% | 1.0% | 3.0% | 3.0% |
| Limonene[2] (hydrocarbon solvent) | 5.0% | 5.0% | 5,0% | 5.0% |
| Alcohol, C12-C15, ethoxylated [3] | 1.0% | 3.0% | 3.0% | 3.0% |
| Tall oil fatty acid[4] | 3.2% | 3.2% | 1.2% | 3.2% |
| Polydimethylsiloxane fluid[5] | 3.0% | 1.5% | 0% | 0% |
| Carnauba wax[6] | 0% | 0% | 1% | 0% |
| PH | 5 | 5 | 5 | 5 |
| Deionized water | Balance | Balance | Balance | Balance |

[1]Modified polysaccharide according to the invention (e.g, Sample 1 or Sample 2 above).
[2]Available from Sigma Aldrich, St. Louis, Missouri USA.
[3]NEODOL ® 25-7, available from Shell Chemicals, Houston, Texas USA.
[4]XTOL ® 100 Tall Oil Fatty Acid, available from Georgia-Pacific Chemicals, Atlanta, Georgia USA.
[5]XIAMETER ® Polydimethylsiloxane (PDMS) Fluids, available from available from Dow Corning, Midland, Michigan USA.
[6]Available from the Frank B. Ross Co., Rahway, New Jersey USA.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A modified polysaccharide having both cationic and silicon substituents, the modified polysaccharide being cationically substituted by quaternary ammonium groups and having a charge density of about 0.1 to about 2.5 meq/g, the modified polysaccharide further being substituted by siliconate groups so that the modified polysaccharide has a silicon content of about 300 to about 5000 ppm.

2. The modified polysaccharide according to claim 1, wherein the quaternary ammonium groups are derived from a quaternary ammonium compound of one of the general formulae (I) or (II):

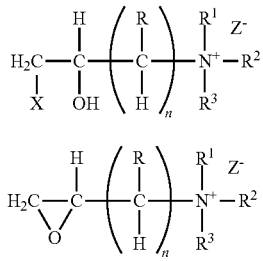

wherein
n is an integer from 1 to 16;
X is halogen;
Z⁻ is an anion which may be inorganic, nitrate, nitrite; phosphate, sulfate or hydroxide; or organic;
R is hydrogen or methyl; and
$R^1$, $R^2$ and $R^3$ are independently an organic radical having up to 10 carbon atoms.

3. The modified polysaccharide according to claim 1, wherein the polysaccharide is crosslinked to reduce its solubility in water.

4. The modified polysaccharide according to claim 1, wherein the ratio of cationic substituents to silicon substituents on the polysaccharide is from about 1500:1 to about 1:3.

5. The modified polysaccharide according to claim 1, wherein the polysaccharide is a starch.

6. The modified polysaccharide according to claim 5, wherein the starch is chosen from banana, corn, pea, potato, sweet potato, barley, wheat, rice, sago, amaranth, tapioca, sorghum, waxy maize, waxy rice, waxy potato, waxy sorghum, waxy cassava, waxy barley, high amylose starch and combinations thereof.

7. The modified polysaccharide according to claim 1, wherein the polysaccharide is a polygalactomannan.

8. The modified polysaccharide according to claim 7, wherein the polygalactomannan is chosen from fenugreek gum, guar gum, tara gum, locust bean gum and cassia gum.

9. The modified polysaccharide according to claim 8, wherein the polygalactomannan is guar gum.

10. The modified polysaccharide according to claim 1, wherein the polysaccharide is substituted by quaternary ammonium groups having a charge density of about 0.2 to about 2.0 meq/g.

* * * * *